United States Patent [19]

Dewanckele et al.

[11] Patent Number: 5,449,595
[45] Date of Patent: Sep. 12, 1995

[54] METHOD FOR MAKING DIRECT-POSITIVE PHOTOGRAPHIC IMAGES

[75] Inventors: Jean-Marie Dewanckele, Drongen; David Terrell, Lint; Kris Viaene, Bonheiden, all of Belgium

[73] Assignee: Agfa-Gevaert, N.V., Mortsel, Belgium

[21] Appl. No.: 267,410

[22] Filed: Jun. 29, 1994

[30] Foreign Application Priority Data

Jul. 12, 1993 [EP] European Pat. Off. ............ 93202051

[51] Int. Cl.$^6$ ................................................. G03C 5/50
[52] U.S. Cl. ..................................... 430/410; 430/378; 430/547; 430/589; 430/598; 430/940
[58] Field of Search ............... 430/264, 265, 378, 406, 430/410, 547, 589, 598, 940

[56] References Cited

U.S. PATENT DOCUMENTS

| | | | |
|---|---|---|---|
| 4,996,137 | 2/1991 | Inoue et al. | 430/598 |
| 5,254,443 | 10/1993 | Kok et al. | 430/598 |
| 5,306,608 | 4/1994 | Kato | 430/547 |

Primary Examiner—Hoa Van Le
Attorney, Agent, or Firm—Breiner & Breiner

[57] ABSTRACT

The present invention relates to a method for making direct-positive photographic images by developing light-sensitive materials in the presence of development nucleators which do not cause loss of sensitivity during exposure or unevenness of development. More specifically the invention relates to the formation of direct-positive images having a high maximum density and high exposure latitude and to photographic materials for use in said formation, which is accomplished by a method for making direct-positive images comprising:

image-wise exposing a photographic light-sensitive silver halide material comprising a support and a layer of an internal latent image-type silver halide emulsion, the pAg of which has been adjusted to a pAg-value between 9.0 and 10.5 inclusive before coating, and developing said exposed photographic silver halide material in a surface developer in the presence of a development nucleator with a group promoting adsorption to silver halide.

It has been found that in a particular embodiment of this invention a development-nucleating amount of a hydrazine compound with a 7-hydroxy-s-triazolo-[1,5-a]-pyrimidine group as group promoting adsorption to silver halide is very useful.

5 Claims, No Drawings

METHOD FOR MAKING DIRECT-POSITIVE PHOTOGRAPHIC IMAGES

DESCRIPTION

1. Field of the Invention

The present invention relates to a method for making direct positive photographic images by developing light-sensitive materials in the presence of development nucleators which do not cause loss of sensitivity during exposure or unevenness of development. More specifically the invention relates to the formation of direct-positive images having a high maximum density and high exposure latitude and to photographic materials for use in said formation.

2. Background of the Invention

In silver halide photography a photographic method, according to which a positive image is made without the use of a negative image or an intermediary process producing a negative image, is called a direct-positive method and a photographic light-sensitive element and a photographic emulsion for use according to such direct-positive method are called direct-positive element and direct-positive emulsion respectively.

A variety of direct-positive photographic methods are known. The most useful methods are the method, which comprises exposing prefogged silver halide grains to light in the presence of a desensitizing agent and developing them and the method, which comprises subjecting a silver halide emulsion that has light-sensitive specks mainly inside the grains to an image-wise exposure and developing the exposed emulsion in the presence of a development nucleator. The present invention relates to the latter method.

A silver halide emulsion comprising light-sensitive specks mainly inside the grains and which forms latent images mainly inside the grains is referred to as internal latent image-type silver halide emulsion, and thus is distinguished from silver halide grains that form latent images mainly at the surface of the grains.

It is known to develop a latent image that has been formed mainly inside the grains by means of a so-called internal developer, but the method, material and emulsions used in accordance with the present invention are not concerned with that type of development, but rather with the type of development using a so-called surface developer.

Methods for making a direct-positive image by development of an exposed internal latent image type-silver halide emulsion in the presence of a development nucleator by means of a surface developer, and photographic emulsions and photographic light-sensitive materials used in such methods have been disclosed in i.a. GB-A 1,011,062, 1,151,363, 1,195,837, in JA Patent Publication No. 29,405/68, and in U.S. Pat. Nos. 2,456,953, 2,497,875, 2,497,876, 2,588,982, 2,592,250, 2,675,318, 3,227,552, 3,761,276, 4,540,655.

In the internal latent image-type method for making a direct-positive image, the development nucleator may be incorporated into a developing solution, but it is usually incorporated into the photographic emulsion layer or in another layer of the photographic light-sensitive material, the development nucleator being adsorbed at the surface of the silver halide grains during development. Development nucleators that can be used in the above-described method for making a direct-positive image include hydrazine and derivatives thereof as described in i.a. "Zeitschrift für Wissenschaftliche Photographie" by Arens, vol. 48, (1953) p.48, DD-A 5024, DE-A 3,021,423, and in U.S. Pat. Nos. 2,563,785, 2,588,982, 3,227,552, 4,245,037, 4,374,923, 4,540,655, in Research Disclosure 23,510, p. 346–348 and the documents referred to therein.

Standard emulsions with development nucleators without a group promoting adsorption to silver halide produce satisfactory images, but migration to the developer may cause uneven development. Migration to the developer can be avoided by using development nucleators with a group promoting adsorption to silver halide. Such nucleators produce nucleation at very low concentrations, but produce an unacceptably high minimum density and rereversal with standard emulsions.

OBJECTS OF THE INVENTION

It is therefore an object of the present invention to provide a method for making direct-positive photographic images by developing photographic light-sensitive silver halide materials in the presence of development nucleators that do not cause unevenness of development.

It is another object of the present invention to provide a photographic light-sensitive silver halide material for forming direct-positive images having a satisfactory high maximum density and low minimum density.

It is a further object of the present invention to provide novel development nucleators.

Other objects of the present invention will become apparent from the description hereinafter.

SUMMARY OF THE INVENTION

It has been found now that the above objects are accomplished by a method for making direct-positive images comprising:
 image-wise exposing a photographic light-sensitive silver halide material comprising a support and a layer of an internal latent image-type silver halide emulsion, the pAg of which has been adjusted to a pAg-value between 9.0 and 10.5 inclusive before coating, and
 developing said exposed photographic silver halide material in a surface developer in the presence of a development nucleator with a group promoting adsorption to silver halide.

It has been found that in a particular embodiment of this invention a development-nucleating amount of a hydrazine compound with a 7-hydroxy-s-triazolo-[1,5-a]-pyrimidine group as group promoting adsorption to silver halide is very useful.

7-hydroxy-s-triazolo-[1,5-a]-pyrimidine group-substituted hydrazine compounds according to this particular embodiment of the invention correspond to one of the general formulae I, II, III and IV:

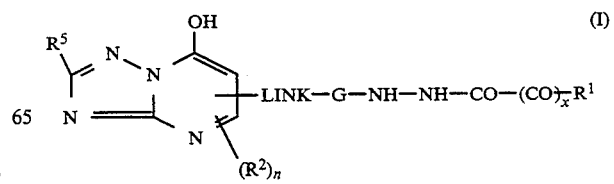

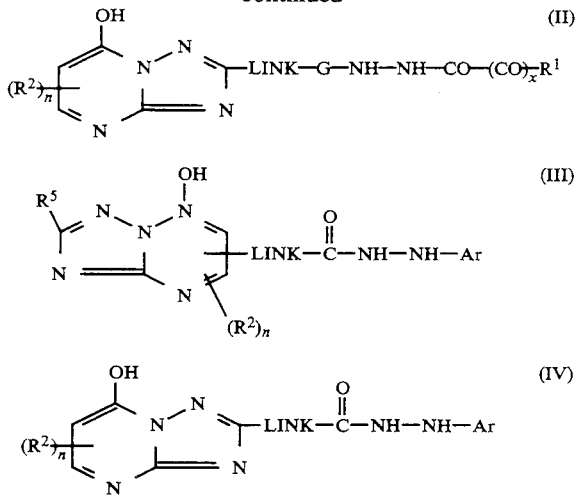

wherein:
LINK stands for a linking member, which can be a chemical bond, a divalent atom e.g. —O— and —S—, or a divalent poly-atom group, e.g. —CH$_2$SCH$_2$CONH—; —SCH$_2$CONH—; —CH$_2$SCH$_2$—; —SCH$_2$—; —CH$_2$—; —NH—; —CO—; —SO$_2$—; —SO$_2$NH—; —NHSO$_2$NH—; —NHCONH—; —CONH— and —NHCO—;

G stands for a bivalent organic group (which can be substituted or unsubstituted) containing at least one homocyclic or heterocyclic aromatic nucleus, e.g. one phenylene group or substituted phonylone group or at least two phenylene groups or substituted phonylone groups that are linked to each other by a chemical bond, a bivalent atom e.g. —O— and —S— or by a bridging group e.g. —SO$_2$—, —N(R$^3$)—; —SO$_2$—N(R$^3$)—, —N(R$^3$)—SO$_2$—, —N(R$^3$)—SO$_2$—N(R$^4$)—, —N(R$^3$)—CO—, —CO—N(R$^3$)—, —N(R$^3$)—CO$_2$—N(R$^4$)—, —(CH$_2$)$_y$—, —(CH$_2$)$_y$—Q—(CH$_2$)$_z$—;

x is 0 or 1;

R$^1$ stands for hydrogen or a monovalent group selected from the group consisting of an alkyl group, a substituted alkyl group, a cycloalkyl group, a substituted cycloalyl group, an alkenyl group, a substituted alkenyl group, an alkynyl group, a substituted alkynyl group, an aralkyl group, a substituted aralkyl group, an aryl group, a substituted aryl group, an alkoxy group, a substituted alkoxy group, an aryloxy group, a substituted aryloxy group, an amino group, a substituted amino group, a heterocyclic group, and a substituted heterocyclic group; and each of R$^2$ and R$^5$ which may be the same or different stands for an alkyl, an alkoxy or a thioalkyl group;

each of R$^3$ and R$^4$ (which may be the same or different) represents hydrogen, a C$_1$-C$_4$ alkyl group e.g. methyl, or an aryl group e.g. phenyl;

Q represents a divalent atom e.g. —O— or —S—;

n is 0 or 1;

m is 0, 1 or 2;

each of y and z independently represents a positive integer from 1 to 5, and

Ar stands for a homocyclic or heterocyclic aromatic nucleus e.g. a phenyl group or a substituted phenyl group, which nucleus may carry one or more substituents (same or different) e.g. chosen from the group consisting of an alkyl group, a substituted alkyl group, a cycloalkyl group, a substituted cycloalkyl group, an alkenyl group, a substituted alkenyl group, an alkynyl group, a substituted alkynyl group, an aralkyl group, a substituted aralkyl group, an aryl group, a substituted aryl group, an alkoxy group, a substituted alkoxy group, an aryloxy group, a substituted aryloxy group, an amino group, a substituted amino group, a heterocyclic group, a substituted heterocyclic group, an alkylthio group, a substituted alkylthio group, an arylthio group, a substituted arylthio group, cyano, a halogen atom e.g. chloro and bromo, carboxy, carbamoyl, a substituted carbamoyl group, hydroxy, nitro, sulpho, sulphamoyl, and a substituted sulphamoyl group.

The present invention also provides a photographic light-sensitive silver halide material for forming direct-positive images, said material comprising a support and in at least one light-sensitive emulsion layer comprising internal latent image-type silver halide grains dispersed in a hydrophilic binder and/or in a hydrophilic colloid layer in water-permeable relationship with the said emulsion layer, at least one nucleating agent with a group promoting adsorption to silver halide, the pAg of said emulsion having been adjusted to a pAg of between 9.0 and 10.5 inclusive before coating.

DETAILED DESCRIPTION OF THE INVENTION

It has been established that by developing in a surface developer in the presence of development nucleators according to the present invention exposed photographic light-sensitive silver halide materials comprising an internal latent image, direct-positive images having a high maximum density can be obtained.

Coating at high pAg-values is believed to reduce the adsorption of nucleation agents with groups promoting adsorption to silver halide during the coating of silver halide emulsions containing such nucleation agents, thereby reducing the desensitization of silver halide emulsions. The presence of 7-hydroxy-s-triazolo-[1,5-a]pyrimidine groups strongly adsorbing to silver halide in the nucleation agent of the present invention results in strongly enhanced nucleation activity during development, thereby either reducing the concentration of nucleation agent for development in conventional surface developers for hydrazine development nucleators with pH values of ca. 11.5 or obtaining surface development at lower pH values of conventional negative developers such as those used for negative microfilms for source document applications with pH values lower than 11.0.

The hydrazines corresponding to the general formulae I to IV are believed to be novel compounds and the present invention also includes such compounds per se.

According to the present invention it is important that in the photographic light-sensitive silver halide for forming direct-positive images, said material comprising a support and in at least one light-sensitive emulsion layer comprising unfogged internal latent image-type silver halide grains dispersed in a hydrophilic binder and/or in a hydrophilic colloid layer in water-permeable relationship with the said emulsion layer, development-nucleating amounts of at least one of the said nucleating agents with a group promoting adsorption to silver halide, the pAg of said emulsion is adjusted to a pAg of at least 9.0 before coating.

Representatives of development nucleators according to the present invention are the following compounds corresponding to the general formulae I, II, III or IV are:

scheme 1, for the products belonging to the general formulae I and II, and according to scheme 2 for those belonging to the general formulae III and IV.

Scheme 1

The following reaction scheme and preparation example of compound D01 is representative of the preparation of other development nucleators with the general formulae I and II

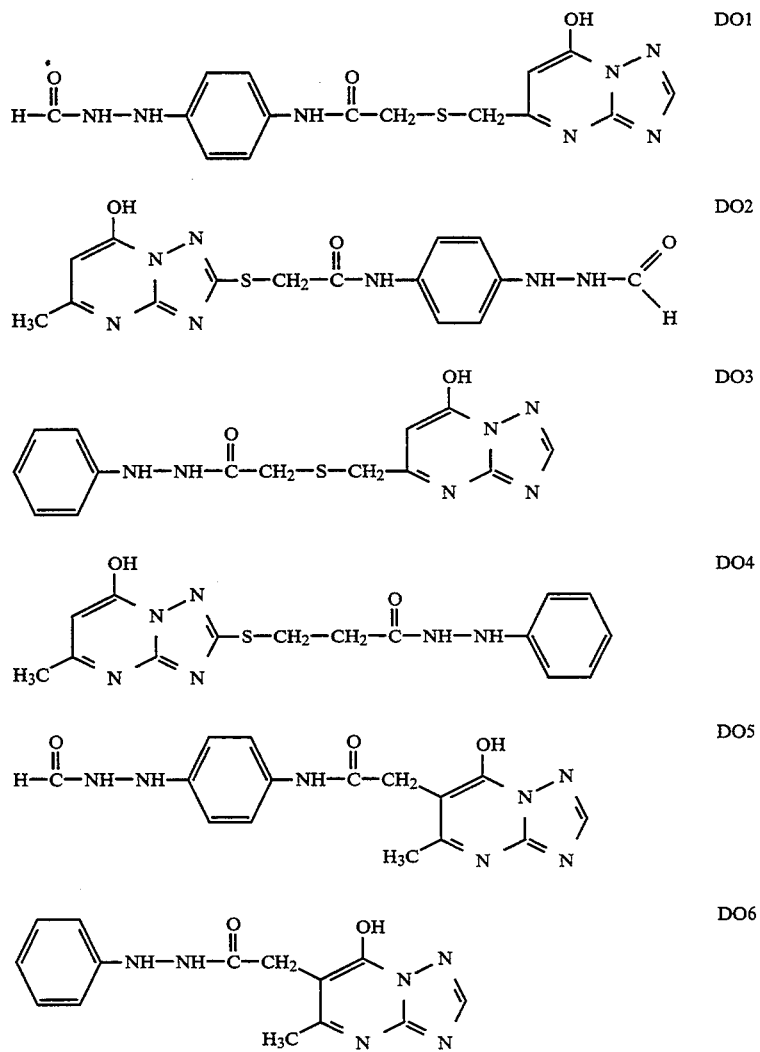

The 7-hydroxy-s-triazolo-[1,5-a]-pyrimidine substituted compounds have been synthesized according to

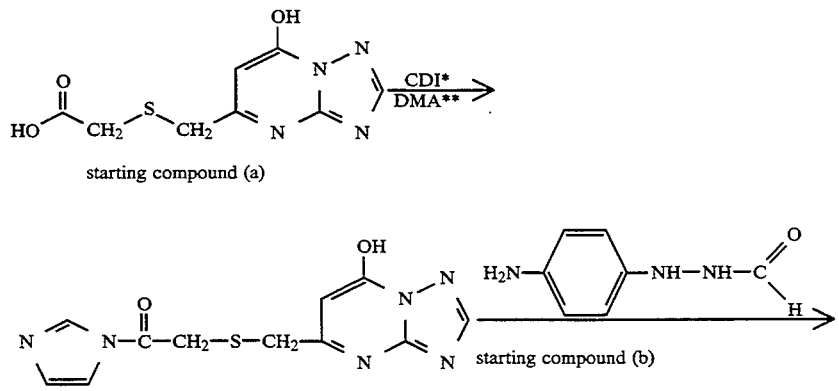

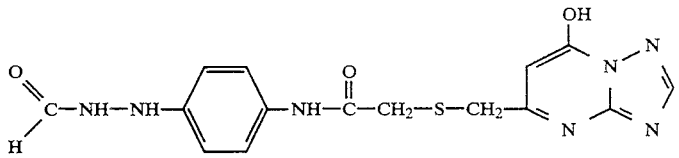

*CDI = 1,1' carbonyldiimidazole
**DMA = N,N'-dimethylacetamide

Starting compound (a) and (c) can be prepared as described in EP-Application 208 346, whereas compound (b) can be prepared as described in DE 3 209 110.

Preparation of D01

An amount of 38.8 g (0.24 mole) of 1,1' carbonyldiimidazole (CDI) was added to a stirred solution of 48 g (0.2 mole) of starting compound (a) in 200 ml of N,N'-dimethylacetamide (DMA). The resulting reaction mixture was stirred for 2 hours at ambient temperature under a nitrogen atmosphere. Next 30.2 g (0.2M) of starting compound (b) in 200 ml DMA was added after which the reaction mixture is stirred for 4 hours. The solution was then concentrated under reduced pressure to 200 ml and poured into 1500 ml of methylene chloride. The precipitate was separated by filtration, washed with a hot mixture of 400 ml isopropanol and 10 ml acetic acid. Yield: 67.8 g of compound D01 melting at 250.2° C.

Scheme 2

The following reaction scheme and preparation example of compound D04 is representative of the preparation of other development nucleators with the general formulae III and IV

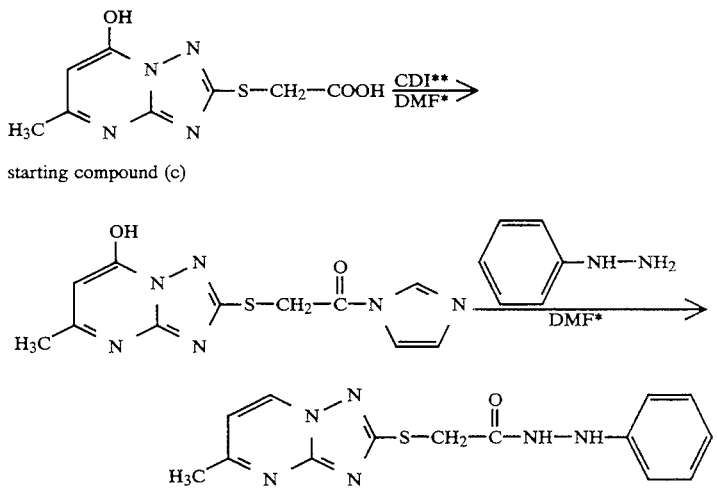

*DMF = N,N'-dimethylformamide
**CDI = 1,1' carbonyldiimidazole

Preparation of D04

An amount of 32.4 g (0.2 mole) of 1,1' carbonyldiimidazole (CDI) was added to a stirred solution of 36 g (0.15 mole) of starting compound (a) in 300 ml of N,N'-dimethylformamide (DMF). The reaction mixture was stirred for 2 hours at ambient temperature under a nitrogen atmosphere. Next 16.2 g (0.15 mole) of phenylhydrazine in 50 ml DMF was added. The reaction mixture was stirred for 12 hours and was then poured out into 3000 ml isopropylacetate. The precipitate was separated by filtration, washed with a mixture of 500 ml water and 25 ml acetic acid at 85° C., filtered and dried. Yield: 37 g of compound D04 melting at 235° C.

The at least one development nucleator used in accordance with the present invention may be incorporated into the developer or in a prebath applied to the exposed photographic material before development thereof. In such an embodiment it is not necessary to increase the coating pAg before coating of the emulsion to a value above 9.0. Preferably, however, the at least one development nucleator is incorporated into the silver halide emulsion layer or into a hydrophilic colloid layer in water-permeable relationship therewith, the pAg of the emulsion being increased to a value above 9.0 before coating.

Mixtures of at least 2 of the above-mentioned development nucleators can be used advantageously.

As mentioned before, nucleating amounts of the development nucleators are present during development of the photographic element and can be incorporated for that purpose e.g. into the light-sensitive silver halide emulsion layer or into a hydrophilic colloid layer in water-permeable relationship therewith. Alternatively, they can also be added to the developing bath or to a separate bath.

When used in the silver halide emulsion layer the development nucleators are present in a concentration of $5 \times 10^{-6}$ mol to $10^{-1}$ mol per mole of silver halide.

Prior to the coating of the composition that will form the photographic layer comprising at least one development nucleator, the development nucleator(s) can be dissolved in an organic solvent and added to said composition. For instance, $1 \times 10^{-5}$ mol of the development nucleator is added in the form of a 0.5% solution in methanol per mol of silver.

According to a preferred embodiment the development nucleator(s) are added in dispersed form to the hydrophilic colloid composition that will form said emulsion layer or said hydrophilic colloid layer. When these hydrazines are present in dispersed form in a hydrophilic colloid layer, preferably in the internal latent image-type silver halide emulsion layer, the direct positive images obtained upon development have a very fine grain.

The development nucleator(s) can be incorporated into the hydrophilic colloid composition that will form said emulsion layer or said hydrophilic colloid layer by dissolving them first in at least one water-immiscible, oil-type solvent or oil-former, adding the resulting solution to an aqueous phase containing a hydrophilic colloid preferably gelatin and a dispersing agent, passing the mixture through a homogenizing apparatus so that a dispersion of the oily solution in an aqueous medium is formed, mixing the dispersion with a hydrophilic colloid composition e.g. a gelatin silver halide emulsion, and coating the resulting composition in the usual manner to produce a system in which particles of development nucleator(s), surrounded by an oily membrane, are distributed throughout the gel matrix. The dissolution of the development nucleator(s) in the oil-former may be facilitated by the use of an auxiliary low-boiling water-immiscible solvent, which is removed afterwards by evaporation.

The development nucleator(s) can be dispersed in hydrophilic colloid compositions with the aid of at least one known oil-former e.g. an alkyl ester of phthalic acid. The oil-formers can be used in widely varying concentrations e.g. in amounts ranging from about 0.1 to about 10 parts by weight and preferably from 0.5 to 2 parts by weight relative to the amount of the development nucleator(s) dispersed therewith.

It may be useful to combine the oil-former with at least one auxiliary solvent that is insoluble or almost insoluble in water and has a boiling point of at most 150° C., such as a lower alkyl acetate e.g. ethyl acetate.

According to a preferred embodiment of the present invention the development nucleator(s) are incorporated into the hydrophilic colloid composition that will form said silver halide emulsion layer or said hydrophilic colloid layer by mixing the development nucleator(s) in the absence of an oil-former and a solvent with an aqueous hydrophilic colloid solution, preferably an aqueous gelatin solution, passing the resulting mixture through a homogenizing apparatus, adding the dispersion obtained to said hydrophilic colloid composition that will form said emulsion layer or said hydrophilic colloid layer, and coating said hydrophilic colloid composition on a support.

The homogenizing apparatus can be any of the devices currently used for making dispersions e.g. an ultrasonic power generator, a mill such as a ball mill, a sand mill, and a colloid mill.

In the photographic light-sensitive direct-positive element according to the present invention the development nucleator(s) is(are) preferably present in the internal latent image-type silver halide emulsion layer. However, the development nucleator(s) can also be incorporated into a hydrophilic colloid layer that stands in water-permeable relationship with the internal latent image-type silver halide emulsion layer e.g. in a protective hydrophilic colloid layer having a thickness of 1 to 3 $\mu$m. The hydrophilic colloid layer can be any layer that is part of the photographic light-sensitive direct-positive element according to the present invention. It can thus be i.a. a light-sensitive layer, an intermediate layer, a filter layer, a protective layer, an antihalation layer, an antistress layer, a subbing layer, or any other layer. In other words, any layer will do provided the development nucleator(s) is(are) not prevented from diffusing to the internal latent image-type silver halide emulsion layer.

The development nucleator(s) used according to the present invention preferably is(are) incorporated into the layer(s) in an amount that yields satisfactory maximum density values of e.g. at least 1.50 when the internal latent image-type emulsion is developed with a surface-developing solution. Depending upon the requirements one or more development nucleators according to this invention can be used in a mixture with at least one non-masked nucleating agent. The amount may vary within wide limits and depends upon the nature of the silver halide emulsion, the chemical structure of the development nucleator(s), and on the developing conditions. Nevertheless, an amount of from about 0.005 to about 15 mmol per mol of silver halide in the internal latent image-type silver halide emulsion is generally effective, more preferably an amount of from about 0.1 to about 9 mmol per mol of silver halide. When the development nucleator(s) is(are) incorporated into a hydrophilic colloid layer that stands in water-permeable relationship with the internal latent image-type silver halide emulsion layer, it is adequate to incorporate the development nucleator(s) in the above amounts while taking into account the amount of silver contained in the associated internal latent image-type emulsion layer.

An internal latent image-type silver halide emulsion is an emulsion, the maximum density of which obtained when developing it with an "internal type" developing solution exceeds the maximum density that is achievable when developing it with a "surface-type" developing solution. Internal latent image-type emulsions that are suited for use in accordance with the present invention have been described in e.g. U.S. Pat. Nos. 2,592,250; 3,206,313; 3,271,157; 3,447,927; 3,511,662; 3,737,313; 3,761,276; GB-A 1,027,146 and JP-Publication No. 34 213/77. However, the silver halide emulsions used in the present invention are not limited to the silver halide emulsions described in these documents.

The internal latent image-type silver halide emulsions that are suited for use in the method of the present invention are emulsions that have not been prefogged externally or only very slightly so and that have not been ripened chemically or only slightly so, as described e.g. in U.S. Pat. Nos. 3,761,276 and 3,850,637.

The photographic emulsions can be prepared according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion" The Focal Press, London (1966).

The photographic silver halide emulsions used in the method of the present invention can be prepared by mixing the halide and silver solutions in partially or fully controlled conditions of temperature, concentrations, sequence of addition, and rates of addition. The silver halide can be precipitated according to the single-jet method, the double-jet method, or the conversion method. The conversion method has proved to be particularly suitable. According to this method a more soluble silver halide is converted into a less soluble silver halide. For instance a silver chloride emulsion is converted in the presence of water-soluble bromide and possibly iodide, the amounts of which are selected with regard to the finally required composition, into a silver chlorobromoiodide or a silver bromoiodide emulsion. This conversion is preferably carried out very slowly in several consecutive steps i.e. by converting a part of the more soluble silver halide at a time. Another technique by which emulsions with an increased internal latent image sensitivity can be prepared has been described in GB-A 1,011,062.

The silver halide particles of the photographic emulsions used in the method of the present invention may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains-may comprise a core and a shell, which may have different halide compositions and/or crystal modifications and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in the method of the present invention.

The average size of the silver halide grains may range from 0.1 to 2.0 μm, preferably from 0.15 to 0.8 μm.

The size distribution of the silver halide particles of the photographic emulsions used in the method of the present invention can be homodisperse or heterodisperse. A homodisperse size distribution is obtained when 95% of the grains have a size that does not deviate more than 30% from the average grain size.

In addition to silver halide the emulsions may also comprise organic silver salts such as e.g. silver benzotriazolate and silver behenate.

The silver halide crystals can be doped with $Rh^{3+}$, $Ir^{4+}$, $Cd^{2+}$, $zn^{2+}$, $pb^{2+}$.

The emulsion can be left unwashed or it can be desalted in the usual ways e.g. by dialysis, by flocculation and re-dispersing, or by ultrafiltration.

The possibly slight chemical sensitization can be performed as described i.a. in the above-mentioned "Chimie et Physique Photographique" by P. Glafkides, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968).

As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB-A 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The nucleating activity of the development nucleators during development can be enhanced by the addition of so-called nucleation accelerators such as polyglycols with dialkyl amino, piperidino or dialkylamino alkylthio end groups such as described in U.S. Pat. No. 4,975,354; or compounds with the general formula P-LNK-N-(Alkyl)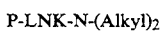

in which P is a group promoting adsorption to silver halide such as

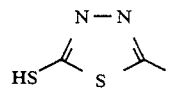

and LNK is a linking group; as described for example in JP-Application 01 224 758.

The spectral photosensitivity of the silver halide can be adjusted by proper sensitization to any desired spectral range comprised between 300 and 900 nm e.g. to blue light of relatively long wavelengths, to green light, to red light, to infrared light, by means of the usual mono- or polymethine dyes such as acidic or basic cyanines, hemicyanines, oxonols, hemioxonols, styryl dyes or others, also tri- or polynuclear methine dyes e.g. rhodacyanines or neocyanines. Such spectral sensitizers have been described by e.g. F. M. Hamer in "The Cyanine Dyes and Related Compounds" (1964) Interscience Publishers, John Wiley & Sons, New York. The spectral photosensitivity of the silver halide can also be adjusted for exposure by laser light e.g. helium-neon laser light, argon laser light, and solid state laser light. Dyes that can be used for adjusting the photosensitivity to laser light have been described in i.a. JA-A 62284344, 62284345, 62141561, 62103649, 62139555, 62105147, 62105148, 62075638, 62062353, 62062354, 62062355, 62157028, 61203446, 62157027, 62113148, 62003250, 60061752, 55070834, 51115821, 51115822, 51106422, 51106423, 51106425; DE-A 3,826,700; U.S. Pat. Nos. 4,501,811, 4,725,532, 4,784,933; GB-A 1,467,638; and EP-A 100,654 and in documents cited therein. The silver halide can also be-sensitized with dyes providing a spectral sensitivity mainly in the range of 400 to 540 nm and not extending the sensitivity substantially beyond 540 nm so that the resulting photosensitive material can be handled in safe-light conditions prior to the image-wise exposure. Suitable dyes that can be used for that purpose have been described in e.g. U.S. Pat. No. 4,686,170.

Other useful sensitizing dyes that can be employed in accordance with the present invention have been described in e.g. U.S. Pat. Nos. 2,503,776, 2,526,632, 3,522,052, 3,556,800, 3,567,458, 3,615,613, 3,615,632, 3,615,635, 3,615,638, 3,615,643, 3,617,293, 3,619,197, 3,625,698, 3,628,964, 3,632,349, 3,666,480, 3,667,960, 3,672,897, 3,677,765, 3,679,428, 3,703,377, 3,705,809, 3,713,828, 3,713,828, 3,745,014, 3,769,025, 3,769,026, 3,770,440, 3,770,449, GB-A 1,404,511, and BE-A 691,807.

The sensitizing dyes employed in the present invention are used in a concentration of from about $1.0 \times 10^{-5}$ to about $5 \times 10^{-3}$ mole per mole of silver halide, and particularly in a concentration of from about $4\times10^{-5}$ to $2\times10^{-3}$ mole per mole of silver halide, as has e.g. been described in EP-A 473 209.

Other dyes, which per se do not have any spectral sensitization activity, or certain other compounds, which do not substantially absorb visible radiation, can have a supersensitization effect when they are incorporated together with said spectral sensitizing agents into the emulsion. Suitable supersensitizers are i.a. heterocyclic mercapto compounds containing at least one electronegative substituent as described e.g. in U.S. Pat. No. 3,457,078, nitrogen-containing heterocyclic ring-substituted aminostilbene compounds as described e.g. in U.S. Pat. Nos. 2,933,390 and 3,635,721, aromatic organic acid/formaldehyde condensation products as described e.g. in U.S. Pat. No. 3,743,510, cadmium salts, and azaindene compounds.

Density-increasing compounds may be incorporated into the photographic light-sensitive direct-positive silver halide element, preferably into an internal latent image-type silver halide emulsion layer thereof, although they may be incorporated also into a hydrophilic colloid layer that stands in water-permeable relationship with the internal latent image-type silver halide emulsion layer. Suitable density-increasing compounds are formic acid, oxalic acid, glyoxylic acid, or salts of these, and polyethylene glycols. When incorporated into the photographic element the density-increasing compound is present in amounts of from 4 to 600 mg/m2, preferably from 40 to 300 mg/m2. When the density-increasing compound is incorporated into a hydrophilic colloid layer it is present therein in the form of a salt e.g. sodium or potassium formate or oxalate.

It is also possible to incorporate the density-increasing compound into a hydrophilic colloid layer that does not stand in direct water-permeable relationship with the internal latent image-type silver halide emulsion layer e.g. because an impermeable support constitutes a barrier between said emulsion layer and said hydrophilic colloid layer. In that case the density-increasing compound can during treatment of the exposed material with a developing solution or a prebath diffuse via said developing solution or said prebath towards the silver halide emulsion layer and have its effect there. Such layers are e.g. layers that have been coated on the rear side of the support and which may serve different purposes. Examples of such layers are e.g. a back layer, an anti-curling layer, and an antistatic layer.

The density-increasing compound may also be added to the developing solution in amounts of from 0.2 to 30 g/l, preferably from 1 to 10 g/l The density-increasing compound may also be added to another processing solution e.g. a prebath when the density-increasing compound is added to the developing solution or to a prebath it is present therein in acid form or in the form of a salt.

A preferred density-increasing compound is oxalic acid, because it has the highest density-increasing effect and can thus be used in lower concentrations.

For processing the photographic element according to the present invention any of the known methods can be employed. Specifically, the processing method used according to the present invention basically includes a development step and a fixing step. A stopping step and a rinsing step can be included as well, if desired. The processing temperature is usually selected within the range of from 18° C. to 50° C. However, temperatures lower than 18° C. and temperatures higher than 50° C. can be employed, if desired. The processing time may vary within broad ranges provided the mechanical strength of the materials to be processed is not adversely influenced and no decomposition takes place.

The developing solution used for developing an exposed photographic element in accordance with the present invention may comprise at least one alkanolamine, which may be chosen from primary, secondary, and tertiary alkanolamines. Suitable alkanolamines are i.a. N,N,N-triethanolamine, 2-amino-2-hydroxymethyl-propan-1,3-diol, N-methyl-diethanolamine, N-ethyl-diethanolamine, diisopropanolamine, N,N-diethanolamine, 3,3'-amino-dipropanol, 2-amino-2-methyl-propan-1,3-diol, N-propyl-diethanolamine, N-butyl-diethanolamine, N,N-dimethyl-ethanolamine, N,N-diethyl-ethanolamine, N,N-diethyl-isopropanolamine, 1-amino-propan-2-ol, N-ethanolamine, N-methyl-ethanolamine, N-ethyl-ethanolamine, N-ethyl-propanolamine, 3-amino-propanol, 3-dimethylamino-propanol, 4-amino-butanol, and 5-amino-pentan-1-ol.

The alkanolamine or a mixture of alkanolamines may be present in the developing solution in amounts of from 1 to 100 g/l, preferably from 10 to 60 g/l.

In the developing solution used in the method of the present invention, a hydroquinone alone or a combination of a hydroquinone with a secondary developing agent of the class of 1-phenyl-3-pyrazolidinone compounds and p-N-methyl-aminophenol can be used as developing agent. Specific examples of hydroquinones include hydroquinone, methylhydroquinone, t-butyl-hydroquinone, chloro-hydroquinone and bromohydroquinone.

Particularly useful 1-phenyl-3-pyrazolidinone developing agents that can be used in combination with a hydroquinone are 1-phenyl-3-pyrazolidinone, 1-phenyl-4-methyl-3-pyrazolidinone, 1-phenyl-4-ethyl-5-methyl-3-pyrazolidinone, 1-phenyl-4,4-dimethyl-3-pyrazolidinone, 1-phenyl-4-hydroxymethyl-4-methyl-3-pyrazolidinone and 4-methyl-4-hydroxymethyl-1-phenyl-3-pyrazolidone.

N-methyl-p-aminophenol and 2,4-diaminophenol can be used in combination with a hydroquinone as a developing agent.

When the secondary developing agent used in the processing method of the present invention is one of the class of the 1-phenyl-3-pyrazolidinone compounds it is preferably present in an amount of 2 to 20 g per liter. When the secondary developing agent is p-N-methyl-aminophenol it is preferably present in an amount of 10 to 40 g per liter.

The developing solution comprises a preservative such as a sulphite e.g. sodium sulphite in an amount ranging from 45 g to 160 g per liter.

The developing solution comprises alkali-providing substances such as hydroxides of sodium and potassium, alkali metal salts of phosphoric acid and/or silicic acid and/or boric acid and/or carbonic acid, e.g. trisodium phosphate, orthosilicates, metasilicates, hydrodisilicates of sodium or potassium, borax, sodium or potassium metaborate, and sodium or potassium-carbonate. The alkali-providing substances can be substituted in part or wholly by alkanolamines.

The developing solution may comprise a buffering agent such as a carbonate e.g. sodium carbonate, potassium carbonate, trisodium phosphate, tripotassium phosphate, disodium hydrogen phosphate, dipotassium hydrogen phosphate, sodium dihydrogen phosphate, potassium dihydrogen phosphate, potassium metaborate, sodium metaborate and borax.

For the purpose of decreasing the formation of fog (Dmin) the developing solution may further contain an inorganic anti-fogging agent such as a bromide e.g. potassium bromide and/or an organic anti-fogging agent such as a benzimidazole e.g. 5-nitro-benzimidazole, a benzotriazole like benzotriazole itself and 5-methyl-benzotriazole.

The developing solution may contain other ingredients such as i.a. toning agents, nucleation accelerators, development accelerators, oxidation preservatives, surface-active agents, defoaming agents, water-softeners, anti-sludge agents, hardeners including latent hardeners, and viscosity-adjusting agents.

Regeneration of the developing solution according to known methods is, of course, possible.

During the preparation of concentrated developer solutions for use in the development of photographic materials according to this invention the problem may arise that, depending on the sequence of the addition of components cited above, a cloudy or turbid solution may be formed if a phosphate buffer and an aminoalcohol are present together in the solution. As flocculation and phase separation between an organic and a water phase have to be avoided at any cost an available preparation method of the developer makes use of the addition of acetic acid in amounts of from 10 to 40 ml per liter of developer solution after the addition of the phosphate buffer and before the addition of the aminoalcohol.

The development may be stopped—though this is often not necessary—with an aqueous solution having a low pH. An aqueous solution having a pH not higher than 3.5 comprising e.g. acetic acid and sulphuric acid, and containing a buffering agent is preferred.

Buffered stop bath compositions comprising a mixture of sodium dihydrogen orthophosphate and disodium hydrogen orthophosphate are preferred.

Conventional fixing solutions may be used. Examples of useful fixing agents include organic sulphur compounds known as fixing agents, as well as a thiosulphate, a thiocyanate, etc. The fixing solution may contain a water-soluble aluminium salt as a hardening agent.

The stopping solution may be an aqueous solution having a low pH. An aqueous solution having a pH not higher than 3.5 comprising e.g. acetic acid and sulphuric acid, and containing a buffering agent is preferred.

Suitable additives for improving the dimensional stability of the photographic element are i.a. dispersions of a water-soluble or hardly soluble synthetic polymer e.g. polymers of alkyl (meth) acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulphoalkyl (meth)acrylates, and styrene sulphonic acids.

Various compounds can be added to the photographic emulsion to prevent the reduction in sensitivity or fog formation during preparation, storage, or processing of the photographic element. A great many compounds are known for these purposes, and they include homopolar or salt-like compounds of mercury with aromatic or heterocyclic rings such as mercaptotriazoles, simple mercury salts, sulphonium mercury double salts and other mercury compounds. Other suitable stabilizers are azaindenes, preferably tetra- or penta-azaindenes, especially those substituted with hydroxy or amino groups e.g. 4-hydroxy-6-methyl-1,3,3a,7-tetra-azaindene. Compounds of this kind have been described by Birr in Z. Wiss. Photogr. Photophys. Photochem. 47, 2–27 (1952). Other suitable stabilizers are i.a. heterocyclic mercapto compounds e.g. 1-phenyl-5-mercaptotetrazole, 3-methyl-benzothiazole, quaternary benzothiazole derivatives, benzotriazole. Specific examples of stabilizers have been mentioned by K. Mees in The Theory of the Photographic Process, 3rd ed. 1966 by reference to the papers that first reported such compounds.

Preferred compounds suitable for use in this invention have further been described in EP-A 527 517.

The silver halide emulsions may comprise other ingredients e.g. development accelerators, wetting agents, and hardeners. The binder of the silver halide emulsion layer and/or of other hydrophilic colloid layers can, especially when the binder used is gelatin, be hardened with appropriate hardening agents such as those of the epoxide type, those of the ethylenimine type, those of the vinylsulfone type e.g. 1,3-vinylsulphonyl-2-propanol, di-(vinylsulphonyl)-methane or ethylene di-(vinyl-sulphone), chromium salts e.g. chromiumacetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxydioxan, active vinyl compounds e.g. 1,3,5-triacryloylhexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts and the phosphorus compounds described in EP published Application N°408 143.

The photographic light-sensitive direct-positive element of the present invention may contain a water-soluble dye in a hydrophilic colloid layer as a filter dye or for other various purposes such as for the prevention of irradiation or anti-halation. Such dyes include oxonol dyes, hemioxonol dyes, styryl dyes, merocyanine dyes, cyanine dyes, and azo dyes. Of these, oxonol dyes, hemioxonol dyes, and merocyanine dyes are useful.

When a hydrophilic colloid layer of the photographic light-sensitive direct-positive element of the present invention contains a dye or an UV-absorbing agent, these compounds may be mordanted by means of a cationic polymer e.g. polymers described in GB-A 1,468,460 and 685,475, U.S. Pat. Nos. 2,675,316, 2,839,401, 2,882,156, 3,048,487, 3,184,309, 3,445,231, and 3,986,875, DE-A 1,914,362.

The photographic light-sensitive direct-positive element of the present invention may comprise various kinds of surface-active agents or plasticizers in the photographic emulsion layer or in at least one other hydrophilic colloid layer. Suitable surface-active agents or plasticizers include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents or plasticizers can be used for various purposes e.g. as coating aids, as compounds for preventing electric charging, as compounds improving slidability, as compounds facilitating dispersive emulsification, as compounds preventing or reducing adhesion, and as compounds improving the photographic characteristics e.g. higher contrast and development acceleration.

Development acceleration can be accomplished with the aid of various compounds, preferably polyalkylene oxide derivatives having a molecular weight of at least 400 such as those described in e.g. U.S. Pat. Nos. 3,038,805, 4,038,075, and 4,292,400.

The photographic light-sensitive direct-positive element of the present invention may further comprise in the silver halide emulsion layer various other additives such as e.g. UV-absorbers, matting agents or spacing agents and lubricants.

Suitable UV-absorbers are i.a. aryl-substituted benzotriazole compounds as described in U.S. Pat. No. 3,533,794, 4-thiazolidone compounds as described in U.S. Pat. Nos. 3,314,794 and 3,352,681, benzophenone compounds as described in JP-A 2784/71, cinnamic ester compounds as described in U.S. Pat. No. 3,705,805 and 3,707,375, butadiene compounds as described in U.S. Pat. No. 4,045,229, and benzoxazole compounds as described in U.S. Pat. No. 3,700,455.

Suitable spacing agents are e.g. finely divided silica particles and polymer beads as described U.S. Pat. No. 4,614,708.

In general, the average particle size of spacing agents is in the range between 0.2 and 10 $\mu$m. Spacing agents can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made i.a. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708.

A matting agent and/or a lubricant may be added to an emulsion layer and/or a protective layer of the photographic light-sensitive direct-positive element of the present invention. Suitable matting agents are e.g. water-dispersible vinyl polymers such as poly(methyl methacrylate) having an appropriate particle size of from 0.2 to 6 $\mu$m and inorganic compounds e.g. silver halide and strontium barium sulphate. The lubricant is used to improve the slidability of the photographic element. Suitable examples of lubricants are e.g. liquid paraffin, waxes such as esters of higher fatty acids, polyfluorinated hydrocarbons or derivatives thereof, silicones such as polyalkylpolysiloxanes, polyarylpolysiloxanes, polyalkylarylpolysiloxanes and alkyleneoxide addition derivatives thereof.

The protective hydrophilic layer of the photographic light-sensitive direct-positive material of the present invention preferably is a gelatin layer that also comprises silica as a spacing agent and of one of the abovementioned plasticizers.

A variety of photographic supports can be employed for the photographic light-sensitive direct-positive element of the present invention. The silver halide emulsion can be coated onto one side or both sides of the support.

Suitable supports are e.g. cellullose acetate films such as cellulose triacetate film and cellulose diacetate film, cellulose nitrate films, polyethylene terephthalate films and polystyrene films.

In a first step for making a direct-positive image the photographic light-sensitive silver halide material is exposed image-wise. This exposure can either be a high-intensity exposure such as a flash exposure or a normal intensity exposure such as a daylight exposure, a low-intensity exposure such as an exposure by means of a printer, or an exposure of even lower intensity. The light source used for the exposure should match the wavelength sensitivity of the light-sensitive material. Natural light (sunlight), the light emitted by an incandescent lamp, a halogen lamp, a mercury vapour-lamp, a fluorescent tube, an electronic flash lamp, or by a metal-burning flash bulb can be used. Gas-, dye- or semiconductor lasers emitting light in the wavelength ranges from ultraviolet to infrared as well as a plasma light source are also suitable light sources for exposing the photographic light-sensitive silver halide material for use in the method of the present invention. A line-shaped light source or a planar light source as well as an arrangement with a fluorescing area (CRT, etc.), the fluorescence of which is produced by fluorescing substances stimulated by means of electron rays, or even a liquid-crystal display (LCD) or a lanthanum-doped lead-titanium zirconate (PLZT) can be used as well as light sources for exposing the photographic light-sensitive silver halide material for use in the method of the present invention. If necessary, the spectral distribution of the exposure light can be controlled by means of a colour filter.

In a second step for making a direct-positive image the image-wise exposed silver halide material is soaked with, e.g. immersed in, a developing solution. For instance, the image-wise exposed silver halide material is conducted through a tray containing a developing solution.

The developing agents may be incorporated partially or completely into the photographic light-sensitive silver halide material. They may be incorporated during the preparation stage of the material or at a later stage by means of a processing liquid with which the photographic material is wet prior to the development of the direct-positive image. In this way the surface developer can be reduced to a mere alkaline liquid that is substantially free from developing agents. Such an alkaline aqueous liquid, often called "activator" offers the advantage of having a longer activity i.e. of being less rapidly exhausted. The preliminary processing liquid may contain at least a part of the development nucleator and may also contain other ingredients that otherwise would have been incorporated into the developing solution. Wetting of the photographic material by means of a processing liquid comprising development nucleator and/or density-increasing compound may be performed according to any conventional method such as by soaking or by moistening one single side of the material e.g. by means of a lick roller, by spreading a paste e.g. contained in a pod, or by spraying.

The photographic light-sensitive silver halide material used in the method of the present invention may serve different purposes. Application fields, in which direct-positive images can be made in accordance with the present invention, are i.a. graphic arts recording processes, silver salt diffusion transfer reversal processes, microfilm recording processes, duplicating processes for cinematographic black-and-white negatives, infrared laser recording processes, X-ray recording processes, cathode-ray recording processes, fototypesetting processes, etc.

The present invention will be explained in greater detail by reference to the following examples. The present invention should, however, not be construed as being limited thereto.

EXAMPLE 1

An emulsion A was prepared in the following manner:

Emulsion A

A silver bromide emulsion of cubic crystal habit with an average grain diameter of 0.24 μm was produced by simultaneous addition of a 2.93M aqueous solutions of potassium bromide and of silver nitrate to a 4.78% by weight solution of gelatin in demineralized water at 60° C. over a period of 40.8 minutes at a pAg of 7.0. Per mole of silver bromide were then added $2.58 \times 10^{-5}$ moles of sodium thiosulfonate, $1.63 \times 10^{-5}$ moles of chloroauric acid and $2.75 \times 10^{-5}$ moles of sodium p-toluene thiosulfonate were than added and the emulsion was chemically sensitized for 2 hours at 60° C. at a pAg of 7.0. The chemically sensitized silver bromide grains thus produced were used as cores for the further precipitation of silver bromide by the simultaneous addition of aqueous 2.93M solutions of potassium bromide and silver nitrate at 60° C. for 20 minutes at a pAg of 7.0, ultimately producing an internally ripened monodisperse core/shell emulsion of cubic silver bromide grains with an average diameter of 0.30 μm. After washing with water and desalting, $1.37 \times 10^{-5}$ moles of sodium thiosulfate, $2.47 \times 10^{-6}$ moles of chloroauric acid, $2.68 \times 10^{-5}$ moles of ammonium thiocyanate and $1.62 \times 10^{-6}$ moles of sodium p-toluene thiosulfonate all per mole of silver bromide were added and chemical sensitization carried out for 3.50 hours at 46° C., a pAg of 7.8 and a pH of 5.2, so giving an internal latent image emulsion A.

Emulsion A was divided into separate parts to which the amounts as indicated in Table 1 of nucleating agents of the present invention and comparative nucleating agents A to F as shown below were added.

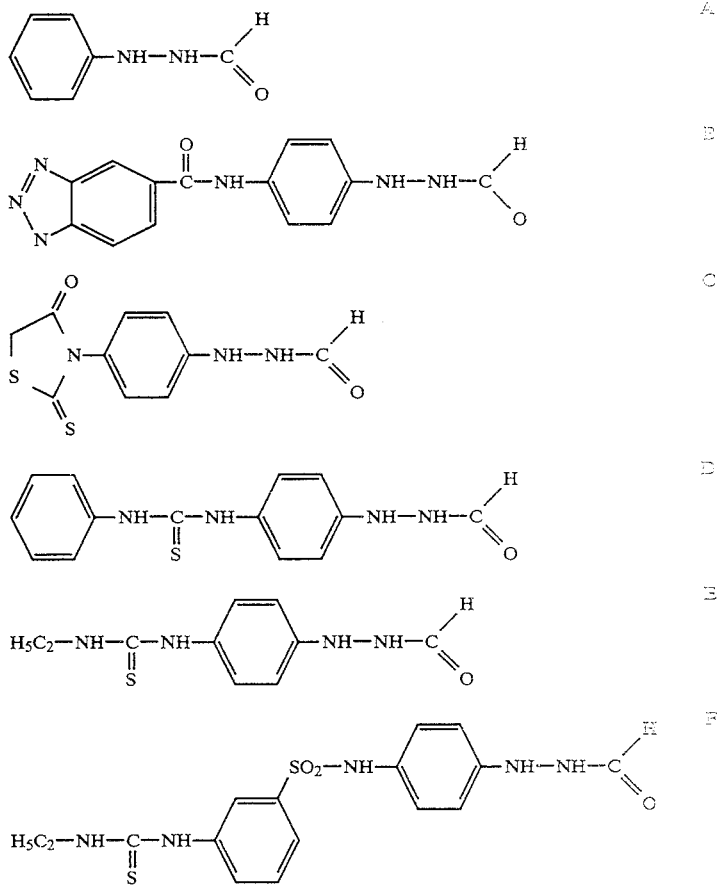

The following ingredients were also added: 1.7 moles per mole of silver bromide of the illustrated compound S01 as a sensitizing dye,

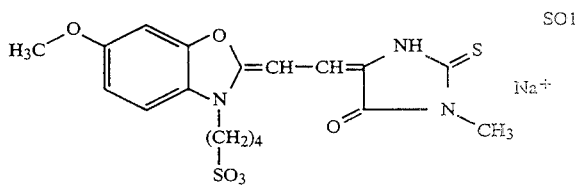

ammonium perfluoro-octanoate as a wetting agent and thickeners so as to achieve the required coating viscosity. In addition a solution of gelatin, ammonium perfluoro-octanoate (as a wetting agent) and formaldehyde (as a hardener) was prepared for the coating of a protective antistress layer.

Samples 1 to 20 were prepared by coating the solution for the protective antistress layer together with the emulsion layer using a simultaneous coating process to give a coated silver bromide quantity of 3.9 g per square meter on a polyethylene terephthalate film. The coating pAg (Coat. pAg) is given in Table 1 for each sample.

These samples were exposed for $1 \times 10^{-5}$ s with a xenon flash light source (supplied by EG&G Inc., 45 William Street, Wellesley, Ma. 02181, USA) through a 460U filter via a step wedge and then developed for the times (Dev. Time) given in Table 1 with a hydroquinone-type developing solution at a temperature of 35° C., said solution comprising the following ingredients:

| | |
|---|---|
| demineralized water | 500 mL |
| hydroquinone | 40 g |
| N-methyl-p-aminophenol sulfate | 15 g |
| sodium sulphite | 110 g |
| sodium hydroxide | 19 g |
| sodium carbonate | 40 g |
| sodium bromide | 3 g |
| 2-methylaminoethanol | 40 mL |
| Tetrasodium salt of ethylenediamine tetra acetic acid | 1 g |
| demineralized water to make | 1 L (pH-value: 11.3) |

The Dmax and Dmin values, the speed (evaluated at a density level of 0.1 above Drain) and the exposure latitude (evaluated at a density of 0.1 above Dmin.) obtained with the samples are listed in Table 1. The values for speed are expressed in log E: the higher the speed value, the lower the speed. In Table 1 the concentration of the nucleating agent (Conc. Nucl. Agent) is expressed in μmole per 100 g of silver nitrate. The exposure latitude (Exp. Lat.) is given for a density of 0.1 above Dmin.

TABLE 1

| Sample No. | Nucl. Agent | Conc. Nucl. Agent | Coat. pAg | Dev. Time (s) | Dmax | Dmin | Speed | Exp. Lat. |
|---|---|---|---|---|---|---|---|---|
| 1 | A | 3900 | 8.6 | 35 | 2.10 | 0.20 | 1.65 | 0.70 |
| 2 | B | 10 | 8.6 | 40 | 2.15 | 0.37 | 1.75 | 0.60 |
| 3 | C | 50 | 8.6 | 30 | 2.60 | 0.34 | 1.76 | 0.55 |
| 4 | D | 10 | 8.6 | 60 | 2.00 | 0.50 | 1.65 | 0.60 |
| 5 | E | 50 | 8.6 | 15 | 2.40 | 0.23 | 1.70 | 0.55 |
| 6 | F | 10 | 8.5 | 25 | 2.10 | 0.16 | 1.60 | 0.95 |
| 7 | D01 | 10 | 8.5 | 30 | 2.30 | 0.47 | | |
| 8 | D01 | 10 | 9.0 | 30 | 2.20 | 0.32 | | |
| 9 | D01 | 10 | 9.5 | 35 | 2.10 | 0.16 | | |
| 10 | D01 | 10 | 10.0 | 35 | 2.00 | 0.13 | | |
| 11 | D01 | 10 | 10.5 | 45 | 2.10 | 0.26 | | |
| 12 | D01 | 10 | 11.0 | 50 | 2.25 | 0.92 | | |
| 13 | D01 | 10 | 11.5 | 30 | 2.05 | 0.20 | | |
| 14 | D01 | 100 | 8.5 | 15 | 2.05 | | | |
| 15 | D01 | 100 | 10.0 | 20 | 2.30 | | | |
| 16 | D02 | 10 | 8.5 | 30 | 2.15 | 0.55 | 1.75 | >1.25 |
| 17 | D02 | 10 | 10 | 40 | 1.58 | 0.18 | 1.55 | 0.80 |
| 18 | D02 | 50 | 10 | 25 | 2.45 | 0.14 | 1.75 | >1.25 |
| 19 | D02 | 100 | 10 | 20 | 2.00 | 0.16 | 1.65 | 1.05 |
| 20 | D04 | 500 | 8.5 | 60 | 1.80 | 0.78 | 1.55 | 0.45 |

As can be seen from Table 1 especially the development nucleators D01 and D02 used in accordance with this invention provide a high sensitivity, a high exposure latitude, a high maximum density and a low minimum density (low re-reversal level, especially at higher pAg values up to pAg 10.5) for low concentrations of the said development nucleators, present in the coated emulsion layer of the photographic materials. As no migration of the said development nucleator occurs, there is no detectable unevenness in the direct-positive image obtained after the processing of said materials.

EXAMPLE 2

The samples 21 to 25 were cast as described in Example 1 except that the sensitizing dyes (sensi) S02 and S03 with the following formulae

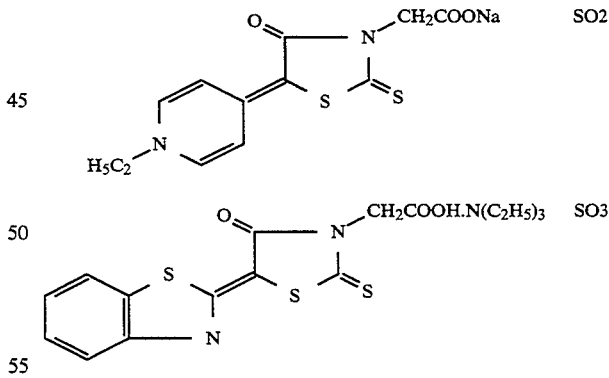

were used instead of S01 at the concentrations (conc. sensi) specified in Table 2 in mmoles per mole of silver nitrate. The nucleating agents (nucl. agent) used together with the coating pAg (coat. pAg) are also given in Table 2. The resulting materials were evaluated as described in Example 1 and the results are given in Table 2.

TABLE 2

| Sample No. | Nucl. Agent/ Sens. | Conc. Nuc. Ag/ Sensi | Coat. pAg | Dev. Time (s) | Dmax | Dmin | Speed | Exp. Lat. |
|---|---|---|---|---|---|---|---|---|
| 21 | A/S02 | 3900/1.0 | 8.6 | 35 | 2.15 | 0.17 | 1.80 | 0.65 |
| 22 | D02/S02 | 10/1.0 | 10.0 | 60 | 1.95 | 0.08 | 1.75 | 1.00 |

TABLE 2-continued

| Sample No. | Nucl. Agent/ Sens. | Conc. Nuc. Ag/ Sensi | Coat. pAg | Dev. Time (s) | Dmax | Dmin | Speed | Exp. Lat. |
|---|---|---|---|---|---|---|---|---|
| 23 | D02/S03 | 10/1.5 | 10.0 | 50 | 2.50 | 0.08 | 1.55 | 0.90 |
| 24 | A/S03 | 3900/1.0 | 8.6 | 45 | 2.15 | 0.12 | 1.55 | 0.65 |
| 25 | D02/S03 | 10/1.0 | 10.0 | 60 | 2.15 | 0.08 | 1.60 | 1.00 |

As can be seen from Table 2 especially the development nucleator D02 used in accordance with this invention, combined with sensi S02, provides a high sensitivity, a high exposure latitude, a high maximum density and a low minimum density (low re-reversal level, especially at higher pAg values up to pAg 10) for low concentrations of the said development nucleators, present in the coated emulsion layer of the photographic materials.

We claim:

1. Photographic light-sensitive silver halide material, said material comprising a support and in at least one light-sensitive emulsion layer comprising internal latent image-type silver halide grains dispersed in a hydrophilic binder and/or in a hydrophilic colloid layer in water-permeable relationship with the said emulsion layer, at least one development nucleating agent which is a hydrazine compound with a 7-hydroxy-s-triazolo-[1,5-a]-pyrimidine group the pAg of said emulsion having been adjusted to a pAg of between 9.0 and 10.5 inclusive before coating.

2. Photographic material according to claim 1 wherein the said development-nucleating agent is used in amounts of from $5 \times 10^{-6}$ to $10^{-1}$ mole per-mole of silver halide present.

3. A photographic material according to claim 1, wherein said development nucleator has been added in dispersed form to the hydrophilic colloid composition that will form said emulsion layer or a hydrophilic colloid layer in water-permeable relationship therewith.

4. Photographic material according to claim 1 wherein said development-nucleating agent with a 7-hydroxy-s-triazolo-[1,5-a]-pyrimidine group corresponds to one of the general formulae (I) to (IV) as follows:

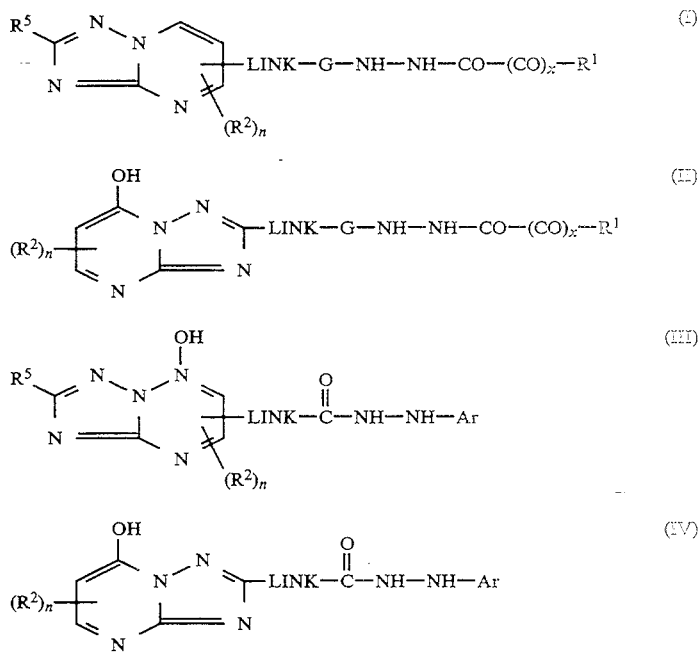

wherein:

LINK stands for a linking member, which can be a chemical bond, —O—, —S—, or a divalent polyatom group selected from the group consisting of —CH$_2$SCH$_2$CONH—; —SCH$_2$CONH—; —CH$_2$SCH$_2$—; —SCH$_2$—; —CH$_2$; —NH—; —CO—; —SO$_2$—; —SO$_2$NH—; —NHSO$_2$NH—; —NHCONH—; —CONH— and —NHCO—;

G stands for a bivalent organic group containing at least one phenylene group or at least two phenylene groups that are linked to each other by a chemical bond selected from the group consisting of —O—, —S—, —SO$_2$—; —N(R$^3$)—; —SO$_2$—N(R$^3$)—, —N(R$^3$)—SO$_2$, —N(R$^3$)—SO$_2$—, N(R$^4$)—, —N(R$^3$)—CO—, —CO—N(R$^3$)—, N(R$^3$)—CO—N(R$^4$), —(CH$_2$)$_y$—, —(CH$_2$)$_y$—Q—(CH$_2$)$_z$—;

R$^1$ stands for hydrogen or a monovalent group selected from the group consisting of an alkyl group, a cycloalkyl group, an alkenyl group, an alkynyl group, an aralkyl group, an aryl group, an alkoxy group, an aryloxy group, an amino group, and a heterocyclic group; and each of R$^2$ and R$^5$ which may be the same or different stands for an alkyl, an alkoxy or a thioalkyl group; each of R$^3$ and R$^4$ which may be the same or different represents hydrogen, a C$_1$-C$_4$ alkyl group, or an aryl group; Q represents —O— or —S—;

n is 0 or 1;

m is 0, 1 or 2;

x is 0 or 1;

each of y and z independently represent a positive integer from 1 to 5; and Ar stands for a homocyclic or heterocyclic aromatic nucleus.
5. Photographic material according to claim 1 wherein said development-nucleating agent corresponds to the formula
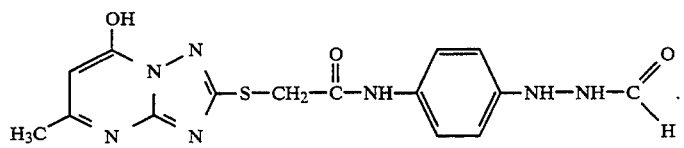
* * * * *

UNITED STATES PATENT AND TRADEMARK OFFICE
CERTIFICATE OF CORRECTION

PATENT NO. : 5,449,595

DATED : September 12, 1995

INVENTOR(S) : Jean-Marie Dewanckele et al

It is certified that error appears in the above-indentified patent and that said Letters Patent is hereby corrected as shown below:

Column 3, line 33, "substituted phonylone" should read
-- substituted phenylene --;

Column 3, lines 34/35, "substituted phonylone groups" should read -- substituted phenylene groups --;

Column 11, line 24, "grains-may comprise" should read
-- grains may comprise --;

Column 11, line 45, "zn$^{2+}$, pb$^{2+}$" should read -- Zn$^{2+}$, Pb$^{2+}$ --;

Column 13, line 51, "10 g/l The" should read --10 g/l. The--;

Column 13, line 53, "a prebath when" should read
-- a prebath. When --;

Column 20, formula B, the terminal group "$-C\begin{smallmatrix}H\\O\end{smallmatrix}$"
should read -- $-C\begin{smallmatrix}H\\O\end{smallmatrix}$ --;

Column 21, line 55, "0.1 above Drain)" should read
-- 0.1 above Dmin) --;

Column 22, TABLE 1, column heading Speed, third numeral down
"1.76" should read -- 1.75 --;

UNITED STATES PATENT AND TRADEMARK OFFICE
CERTIFICATE OF CORRECTION

PATENT NO. : 5,449,595
DATED : September 12, 1995
INVENTOR(S) : Jean-Marie Dewanckele et al It is certified that error appears in the above-indentified patent and that said Letters Patent is hereby corrected as shown below:

Claim 4, column 24, Formula I, a hydroxy group should be attached to the benzene ring as follows:

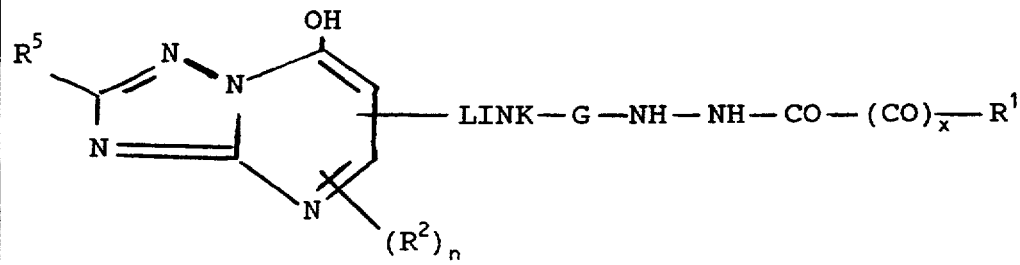

Signed and Sealed this

Tenth Day of September, 1996

Attest:

BRUCE LEHMAN

Attesting Officer

Commissioner of Patents and Trademarks